United States Patent
Winsor et al.

(10) Patent No.: US 7,092,581 B2
(45) Date of Patent: Aug. 15, 2006

(54) BALANCING AREAS OF VARYING DENSITY IN A DIGITAL IMAGE

(75) Inventors: Robin Winsor, Calgary (CA); Arunas Salkauskas, Calgary (CA)

(73) Assignee: Imaging Dynamics Company Ltd., Calgary (CA)

( * ) Notice: Subject to any disclaimer, the term of this patent is extended or adjusted under 35 U.S.C. 154(b) by 786 days.

(21) Appl. No.: 10/302,821

(22) Filed: Nov. 25, 2002

(65) Prior Publication Data

US 2003/0118226 A1   Jun. 26, 2003

Related U.S. Application Data

(60) Provisional application No. 60/333,224, filed on Nov. 23, 2001, provisional application No. 60/333,252, filed on Nov. 23, 2001, provisional application No. 60/333,207, filed on Nov. 23, 2001, provisional application No. 60/333,206, filed on Nov. 23, 2001.

(51) Int. Cl.
*G06K 9/36* (2006.01)

(52) U.S. Cl. .................................. 382/274; 382/276
(58) Field of Classification Search ............. 382/274, 382/276, 283; 399/39, 49; 347/131
See application file for complete search history.

(56) References Cited

U.S. PATENT DOCUMENTS

| | | | | |
|---|---|---|---|---|
| 5,083,160 A * | 1/1992 | Suzuki et al. | ............... | 399/39 |
| 5,298,943 A * | 3/1994 | Ide et al. | ............... | 399/39 |
| 6,219,076 B1 * | 4/2001 | Sato | ............... | 347/131 |
| 6,650,849 B1 * | 11/2003 | Shimura | ............... | 399/49 |
| 6,757,444 B1 * | 6/2004 | Matsugu et al. | ............ | 382/283 |

\* cited by examiner

*Primary Examiner*—Sanjiv Shah
(74) *Attorney, Agent, or Firm*—Gowling Lafleur Henderson LLP; D. Doak Horne; Brian Lee

(57) ABSTRACT

A method for balancing areas of varying density within a digital image, and a computer readable storage medium encoded with the method comprise determining a pixel enhanced intensity value by dividing a pixel unequalized intensity value by a pixel mask intensity value, then scaling the dividend by an exposure compensation factor. The unequalized intensity value is from an unequalized digital image recorded by a digital imaging device. The pixel mask intensity value is proportional to the pixel's blurred intensity value. The exposure compensation factor is selectable by the user and is typically selected as the mean blurred intensity of the pixels.

14 Claims, 2 Drawing Sheets

BALANCING AREAS OF VARYING DENSITY IN A DIGITAL IMAGE

RELATED APPLICATIONS

This application claims priority from and incorporates by reference U.S. application No. 60/333,224 entitled "Lens Assembly and Barrel Correction Method For X-Ray System", U.S. application No. 60/333,252 entitled "Self Diagnostic System for Optically Coupled Digital Radiography", U.S. application No. 60/333,207 entitled "Positioning Stand for a Radiography Imaging Device", and U.S. application No. 60/333,206 entitled "Balancing Areas of Varying Density in a Digital Image", all filed on Nov. 23, 2001.

FIELD OF THE INVENTION

The present invention is directed generally to digital radiography, and in particular to an image processing apparatus, program and method for balancing areas of widely varying density in a digital image.

BACKGROUND OF THE INVENTION

For over a hundred years photographic films have been used to capture and display x-rays for diagnostic purposes. In the last ten years or so, digital radiography has become increasingly popular. Digital radiography refers to the application of digital image processing techniques to projection radiography (x-rays). Digitally recorded x-rays are superior to those recorded with photographic film due to the greater dynamic range of the digital recording system. Furthermore, computer image processing techniques provide a wealth of capabilities to study otherwise obscured details within the image.

To take a digital radiograph, a digital radiography imaging unit is positioned behind a subject. A standard radiographic generator directs radiation through the subject to a fluorescent-imaging screen mounted just behind the front surface of the imaging unit. The imaging screen is the conversion media for radiation to visible light. The fluorescent-imaging screen absorbs the radiographic radiation and emits light of a particular wavelength which closely matches the peak sensitivity of a charge coupled device (CCD) camera. A front-surfaced mirror is positioned at a 45 degree angle inside the imaging unit to direct the radiographic image into the CCD camera. The mirror allows the CCD camera to be positioned out of the direct path of the radiation, effectively shielding it from radiation exposure and prolonging its life. A high-efficiency lens reduces the image and directs it onto the surface of the CCD.

The visual image formed by the fluorescent-imaging screen is converted into a digital image by the CCD sensor. A control computer converts the image into a medical image file that can be viewed for clinical diagnosis, enhanced and electronically stored with the patient demographic information in a picture archiving system.

In a digital radiographic image, it is often desirable to reduce the contrast between various parts of the image so that detailed information in all parts of the image can be viewed at the same brightness and contrast (window level and width) settings. As an example, in a chest radiograph, a patient's ribs may be obscured by differing amounts of soft tissue. The result is that some of the ribs may appear to have lower contrast even though they are the same thickness and density as others.

SUMMARY OF THE INVENTION

According to one aspect of the invention, there is provided an equalization method for balancing areas of varying density within a digital image. The equalization method comprises the following steps:
(a) receiving an unequalized digital image having a plurality of pixels each with an unequalized intensity value;
(b) associating a blurred intensity value to each pixel;
(c) selecting an image enhancement strength factor for the image;
(d) selecting an exposure compensation factor for the image;
(e) determining a mask intensity value for each pixel by calculating the linear convex combination of the pixel's blurred intensity value and the exposure compensation factor, wherein the degree of convex combination is determined by the strength factor;
(f) determining an enhanced intensity value for each pixel by dividing the pixel's unequalized intensity value by the pixel's mask intensity value, and then scaling the dividend by the exposure compensation factor; then
(g) displaying an enhanced image having a plurality of pixels at their enhanced intensity values.

The blurred intensity value for each pixel may be a function of the unequalized intensity values of the pixels in a surrounding kernel. In particular, the blurred intensity value for each pixel may be the average of the unequalized intensity values of the pixels in a surrounding kernel.

The exposure compensation factor may be selected to be the mean blurred intensity value of the image. The mask intensity value may be determined to be the exposure compensation factor*(1−strength factor)+strength factor*blurred intensity value.

According to another aspect of the invention, the equalization method described above may be incorporated into a module of a program encoded on a computer-readable storage medium.

According to another aspect of the invention, there is provided a digital radiography processor that is programmed to balance areas of varying density within a digital image according to the equalization method described above.

According to yet another aspect of the invention, there is provided a method of producing a mask for digital unsharp masking or for digital equalization, comprising:
(a) receiving a starting kernel size K;
(b) receiving a minimum kernel size M;
(c) receiving a number of iterations n;
(d) receiving an unprocessed digital radiograph I;
(e) creating a new image I' by copying I;
(f) creating a new image I, by blurring I' with the kernel;
(g) replacing the pixel values in I' by retrieving the pixel-wise maximum of I, and I;
(h) dividing K by 2; and
(i) repeating steps (f) through (g) for either n iterations or until K is less than or equal to M.

DETAILED DESCRIPTION

Figure 1:
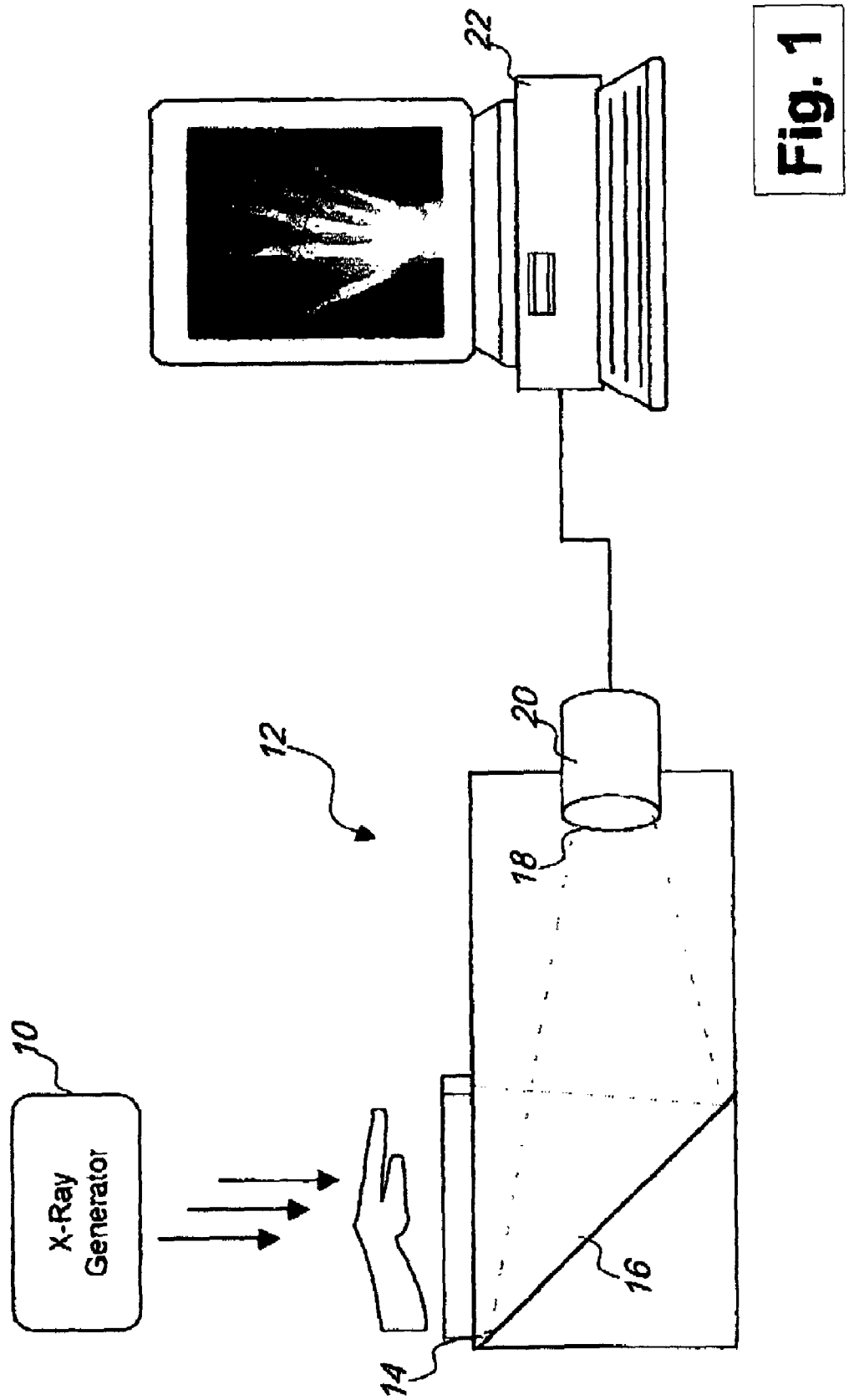
FIG. 1 is a schematic illustration of a digital radiography system having a computer with an image enhancing program that carries out an equalization method on captured unequalized x-ray images.

In one embodiment of the invention, there is provided a digital radiography system that digitally captures an x-ray image and applies to the image a digital equalization method modeled after a method known in the world of analog film processing as unsharp masking.

Analog Unsharp Masking: Photographic film has a higher dynamic range than photographic paper. Therefore, high contrast images captured on a film negative may not display well on a paper print. For example, in a paper print of a person standing inside a darkened room and beside a bright window, the person may appear dark and his details may be obscured, even though the film negative from which the print was developed may have sufficient dynamic range to capture the details of the person. Similarly, a person standing outside and visible through the window may appear so bright that his details may not be clearly visible on the paper print. Special film processing techniques can be applied to bring the details captured on the film negative within the dynamic range of the paper. An example of such a film processing technique is analog unsharp masking. This process helps ease contrast problems in the paper print caused by the film capturing a high contrast image, by balancing areas of widely varying density in the image. It also has the effect of sharpening the resulting image.

Analog unsharp masking involves first creating an underexposed unsharp negative of the original image negative, known as an "unsharp mask". In other words, a washed-out, blurry positive is produced on film. Then, the unsharp mask is overlaid with the original image negative, and the mask and original negative are developed together. This process balances areas of widely varying density in the original image negative, such that when the image is displayed on a paper print, edges and details are enhanced.

This process can be manipulated to vary the appearance of the printed image. For example, the amount of blurring and the degree of underexposure can be independently varied. If the mask is perfectly exposed (no underexposure) and is not blurred, then unsharp masking will produce a perfectly gray picture. If the mask is perfectly exposed and is moderately blurred, then only the edges of the image will be enhanced with the rest of the image being predominantly gray. At the other extreme, where the mask is extremely blurred—so that no shapes are discernable—the masking will serve to even out very broad changes in illumination in the captured image.

This masking process is multiplicative in that the mask attenuates the light coming through the original negative. It does not remove the light by subtraction, since each point attenuates a specific percentage of the light that is incident upon it.

Digital Unsharp Masking: The digital equalization method as described in this embodiment is different from a method known in the art as digital unsharp masking, which contrary to its name, is not precisely analogous to analog unsharp masking. 'Digital unsharp masking' as commonly used in the art is an unfortunate misnomer because the method specifically uses subtraction to apply the mask.

Digital Equalization: The digital equalization method of this embodiment brings details that span a wide dynamic range in a digitally captured image into a narrower, viewable dynamic range as well as enhances fine details in the captured image.

The digital equalization method can be expressed mathematically as follows:

$$I_{E[i,j]} = \frac{F * I_{[i,j]}}{F(1-s) + s * I_{B[i,j]}} \quad (1)$$

wherein

I[i,j] is the unequalized image intensity for a selected pixel at location [i,j] in an image having dimensions [m,n];

$I_E[i,j]$ is the enhanced image intensity for the pixel at [i,j];

$I_B[i,j]$ is the blurred image intensity for the pixel at [i,j] calculated as the mean intensity value of the pixels in a kernel around the pixel [i,j], the kernel having a size selectable by the user (typically between 100×100 and 200×200);

F is the exposure compensation factor, selectable by the user and typically selected as the mean blurred intensity of the pixels.

s is an image enhancement strength factor varying between 0 and 1 (0–100%).

Increasing the strength factor s reduces the contrast of areas in the image having only slight variations in intensity, while simultaneously accentuating areas having high variations in intensity, such as areas of fine detail or edges. Note that if the image enhancement strength factor s is zero, then $$I_{E[i,j]} = F * I_{[i,j]}/F = I_{[i,j]}$$

and no change occurs. This is the digital equivalent to leaving a mask unexposed so that it is uniformly translucent. If, on the other hand the image enhancement factor s is set to 100%. i.e. s=1 and no blurring is applied, $I_{B[i,j]} = I_{[i,j]}$ and:

$$I_E[i,j] = F * I[i,j]/(0 + I[i,j]) = F \text{ for } I[i,j] \neq 0.$$

which is a uniform gray at the selected exposure compensation factor F.

By applying this digital equalization method, information present over a wide dynamic range in a captured digital image can be presented at one time on a computer display, which has a very limited dynamic range, typically capable of displaying only 256 shades of gray at one time. This presents a clear advantage over currently available methods which primarily depend on adjustment of window and level settings to find a best compromise display. Using the digital equalization method, a radiologist can easily see both bony and soft tissue detail in one view, thereby providing a better and faster diagnostic reading of the image.

The digital equalization method is a perfect analog to analog unsharp masking. The denominator of equation (1) is analogous to the pixel intensity of an analog unsharp mask, and can be denoted as $I_{M[i,j]}$:

$$I_{E[i,j]} = \frac{F * I_{[i,j]}}{I_{M[i,j]}} \quad (2)$$

The pixel mask intensity $I_{M[i,j]}$ is thus a convex combination of the pixel's blurred intensity value $I_{B[i,j]}$ and the exposure compensation factor F, and the degree of the convex combination is determined by the strength factor S.

Equation (2) illustrates that, unlike conventional digital unsharp masking, the equalization method is a multiplicative process wherein the pixel enhanced intensity value is determined by dividing the pixel unequalized intensity value by the pixel mask intensity value and scaling the dividend by the exposure compensation factor. As a result, the proportionality of the details relative to their illumination is preserved. For example, consider two ribs that each attenuate 5% of incoming X-radiation, i.e. each have the same density. If one rib is obscured by more soft tissue than the other rib, the unequalized image will show the more obscured rib as having a smaller absolute change in intensity relative than the less obscured rib, even though both ribs have the same density. By applying the equalization method, both ribs will have an increasingly similar absolute brightness (intensity) as the dynamic range is narrowed, i.e. as the image enhancement strength factor is increased. At full equalization (strength factor=100%), ribs of the same density should show the same absolute brightness irrespective of the amount of obscuring material. This is analogous to applying a perfectly exposed blurry mask to a film negative.

A further refinement to the equalization method involves reducing the symmetry of the sharpening effect caused by the equalization method. Typically, when one applies an edge enhancement operator to an image, there is a symmetric enhancement. This means that on the darker side of any edge the image gets darker and on the brighter side, the image gets brighter. This can result in some confusion in digital radiographs, where a dark line could be misinterpreted as a break or as an unusual separation of soft tissue from bone.

A radiographic image is the result of attenuated x-rays. This is in contrast to a photograph that one might take with a hand-held camera, where the light that reaches the film has been reflected from objects in the scene.

The result is that wherever the object or person being imaged is more opaque to x-rays less signal is observed For a digital system this translates into smaller pixel values for objects of interest.

This leads us to the realization that the background in a radiograph typically gives a stronger signal than that obtained from anatomy. Therefore, the following procedure for producing a mask can be used either for digital unsharp masking or for digital equalization:

(a) given a starting kernel size K
(b) given a minimum kernel size M
(c) given a number of iterations n
(d) given an unprocessed digital radiograph I
(e) create a new image I' by copying I
(f) create a new image I, by blurring I' with the 'boxcar kernel' of size K.
(g) replace the pixel values in I' by retrieving the pixel-wise maximum of I, and I.
(h) Divide K by 2.
(i) Repeat steps 6 through 8 for either n iterations or until K<=M.

The equalization method is incorporated into a software program that processes raw x-ray image data captured by a digital x-ray imaging detector. An example of an digital imaging system that includes the detector and a computer that stores the imaging processing program is the Xplorer 1700 digital radiography imaging system manufactured and sold by Imaging Dynamics Company Ltd.

The following description of the method of using the Xplorer system to take an x-ray image of a patient in a hospital illustrates the operation of the equalization method. Referring to FIG. 1:

As soon as a patient is in position and a part of the patient's body selected for imaging has been set in place, an x-ray source 10 is turned on and x-rays are directed towards the patient. X-rays passing through the patient are captured by a detector 12 and converted into a raw digital x-ray image. In particular, the x-ray image reaching the detector 12 is first converted into visible light by a scintillator 14. The visible light is then reflected by a mirror 16 towards a camera lens 18, which reduces and directs the visual image onto the surface of a charge coupled device (CCD) 20, which converts the visual image into a digital image. The digital image is then transferred to a computer 22 which is communicatively linked to the CCD 20. The computer 22 stores the captured raw (unprocessed) digital image in a medical image file, and runs an imaging processing program to process the raw image data into an enhanced form more useful for viewing.

The imaging processing program employs a series of imaging enhancing methods that are applied to enhance the appearance of the captured raw image. First, a series of hardware related corrections are made: A dark field correction method is applied to correct for image noise caused by current generated by the thermal processes within the CCD. This is an additive process. Then, a flat field correction method is employed for correcting for a flat field map of pixel non-uniformity (some pixels will respond to light with a higher output than others). This is a multiplicative process. Then, a barrel correction method is employed for correcting distortion caused by the lens design.

After the hardware related corrections have been made, the program executes a segmentation algorithm to determine which part of the body is being imaged. Then, the program applies an automatic contrast enhancement (the selected enhancement values depending on the part of the body), by mapping the several thousand shades of gray captured by the CCD into the several hundred shades available for display on the computer monitor. Then, a conventional digital unsharp masking method is applied to sharpen certain aspects of the captured image.

Figure 2:
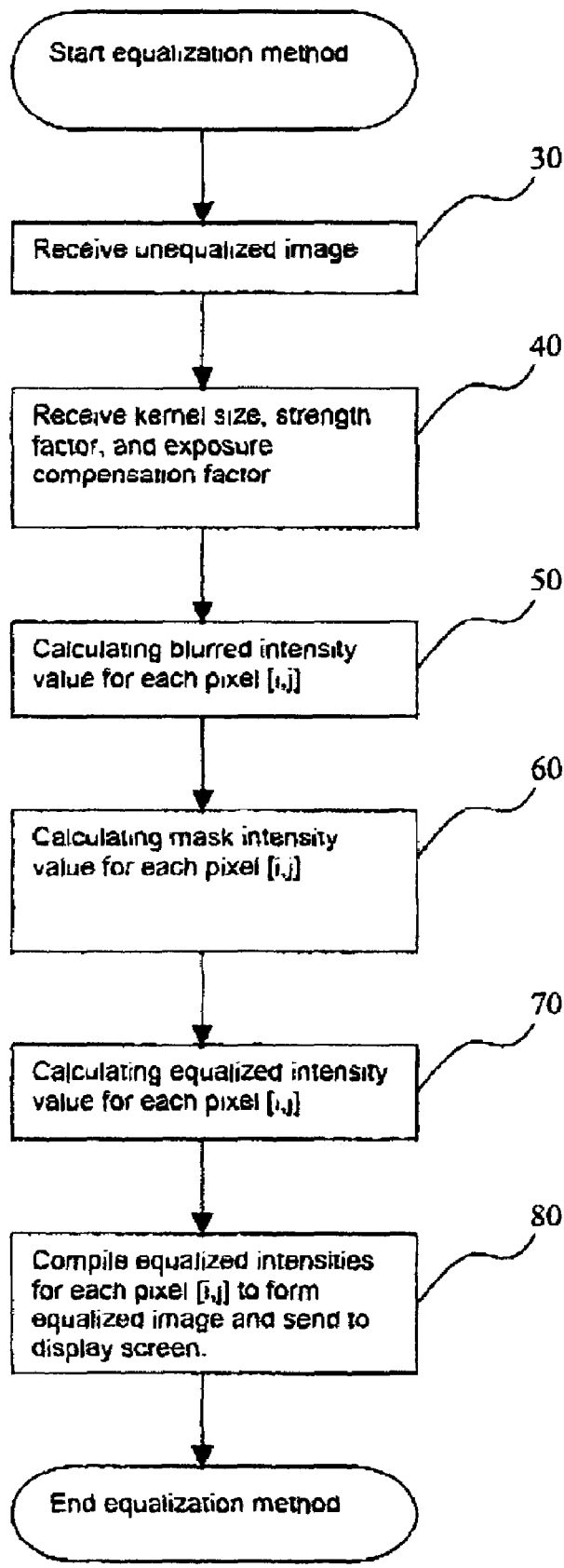
FIG. 2 is a flowchart of the steps performed in the equalization method.

Then, the program executes an equalization method module to balance out the image. Referring to the flowchart in FIG. 2, the method begins by receiving an unequalized digital image as an array of pixels [m,n], wherein each pixel [i,j] in the array [m,n] has an unequalized intensity value I[i,j], as shown in process block 30. The method then receives a number of operator-inputted values, namely: a Kernel size K, an image enhancement strength factor S, and an exposure compensation factor F, as shown in process block 40. The strength factor S may be selected according to the particular anatomy of the body being examined. Some suitable strength factors are:

| | |
|---|---|
| Chest Lateral | 15% |
| Chest PA | 20% |
| Knee | 40% |
| Abdomen | 20% |
| Hand | 50% |
| Extremities | 40–60% |

The method then determines the blurred intensity value $I_{B[i,j]}$ for each pixel [i,j] by calculating the mean unequalized intensity of the pixels in the kernel surrounding the selected pixel [i,j], as shown in process block 50.

Then, the method determines the mask intensity value $I_{M[i,j]}$ for each pixel [i,j] by performing the convex combination calculation: $F*(1-S)+S*I_{B[i,j]}$. This step is shown in process block 60.

Once the mask intensity value has been determined for each pixel, the method determines the enhanced intensity value $I_{E[i,j]}$ of each pixel [i,j], by dividing the pixel's unequalized intensity value $I_{M[i,j]}$ by the pixels mask intensity value $I_{M[i,j]}$, then multiplying the dividend by the exposure compensation factor F. This step is shown in process block 70.

After the enhanced intensity values have been determined for all the pixels, an enhanced image comprising all the enhanced pixels is compiled and sent to a display device (not shown) for display. This step is shown in process block 80.

While the preferred embodiment of the invention has been illustrated and described, it will be appreciated that various changes can be made therein without departing from the scope and spirit of the invention.

What is claimed is:

1. A method of balancing areas of varying density within a digital image, comprising:
    (a) receiving an unequalized digital image from a digital imaging device, the image having a plurality of pixels each with an unequalized intensity value;
    (b) associating a blurred intensity value to each pixel;
    (c) selecting an image enhancement strength factor for the image;
    (d) selecting an exposure compensation factor for the image;
    (e) determining a mask intensity value for each pixel by calculating the linear convex combination of the pixel's blurred intensity value and the exposure compensation factor, wherein the degree of convex combination is determined by the strength factor;
    (f) determining an enhanced intensity value for each pixel by dividing the pixel's unequalized intensity value by the pixel's mask intensity value, and then scaling the dividend by the exposure compensation factor; then
    (g) displaying an enhanced image having a plurality of pixels at their enhanced intensity values.

2. The method of claim 1 wherein the blurred intensity value for each pixel is a function of the unequalized intensity values of the pixels in a surrounding kernel.

3. The method of claim 2 wherein the blurred intensity value for each pixel is the average of the unequalized intensity values of the pixels in a surrounding kernel.

4. The method of claim 1 wherein the exposure compensation factor is the mean blurred intensity value of the image.

5. The method of claim 1 wherein the exposure compensation factor is the mean blurred intensity value of the image, and the mask intensity value is the exposure compensation factor*(1−strength factor)+strength factor*blurred intensity value.

6. The method of claim 5 wherein the blurred intensity value for each pixel is the average of the unequalized intensity values of the pixels in a surrounding kernel.

7. The method of claim 6 wherein in step (f), the exposure compensation factor is multiplied with the dividend.

8. A computer-readable storage medium for execution by a computer, the medium encoded with a module for balancing areas of varying density within a digital image by:
    (a) receiving an unequalized digital image from a digital imaging device, the image having a plurality of pixels each with an unequalized intensity value;
    (b) associating a blurred intensity value to each pixel;
    (c) selecting an image enhancement strength factor for the image;
    (d) selecting an exposure compensation factor for the image;
    (e) determining a mask intensity value for each pixel by calculating the linear convex combination of the pixel's blurred intensity value and the exposure compensation factor, wherein the degree of convex combination is determined by the strength factor;
    (f) determining an enhanced intensity value for each pixel by dividing the pixel's unequalized intensity value by the pixel's mask intensity value, and then scaling the dividend by the exposure compensation factor; then
    (g) displaying an enhanced image having a plurality of pixels at their equalized intensity values.

9. The computer-readable medium of claim 8 wherein the blurred intensity value for each pixel is a function of the unequalized intensity values of the pixels in a surrounding kernel.

10. The computer-readable medium of claim 9 wherein the blurred intensity value for each pixel is the average of the unequalized intensity values of the pixels in a surrounding kernel.

11. The computer-readable medium of claim 8 wherein the exposure compensation factor is the mean blurred intensity value of the image.

12. The computer-readable medium of claim 8 wherein the exposure compensation factor is the mean blurred intensity value of the image, and the mass intensity value is the exposure compensation factor*(1−strength factor)+strength factor*blurred intensity value.

13. The computer-readable storage medium of claim 12 wherein the blurred intensity value for each pixel is the average of the unequalized intensity values of the pixels in a surrounding kernel.

14. The computer-readable storage medium of claim 13 wherein in step (f), the exposure compensation factor is multiplied with the dividend.

* * * * *